US010939893B2

(12) United States Patent
Huang et al.

(10) Patent No.: US 10,939,893 B2
(45) Date of Patent: Mar. 9, 2021

(54) DOPPLER FETAL HEARTBEAT MONITOR

(71) Applicant: Edan Instruments, Inc, Guangdong (CN)

(72) Inventors: Dong Huang, Guangdong (CN); Dewei Chen, Guangdong (CN); Yong Wu, Guangdong (CN)

(73) Assignee: EDAN INSTRUMENTS, INC

( * ) Notice: Subject to any disclaimer, the term of this patent is extended or adjusted under 35 U.S.C. 154(b) by 634 days.

(21) Appl. No.: 15/573,329

(22) PCT Filed: Apr. 10, 2017

(86) PCT No.: PCT/CN2017/079972
§ 371 (c)(1),
(2) Date: Nov. 10, 2017

(87) PCT Pub. No.: WO2018/187915
PCT Pub. Date: Oct. 18, 2018

(65) Prior Publication Data
US 2018/0353153 A1 Dec. 13, 2018

(51) Int. Cl.
*A61B 8/02* (2006.01)
*H05K 5/00* (2006.01)
(Continued)

(52) U.S. Cl.
CPC .............. *A61B 8/02* (2013.01); *A61B 5/00* (2013.01); *A61B 8/0866* (2013.01);
(Continued)

(58) Field of Classification Search
CPC ....... A61B 8/02; A61B 8/4444; A61B 8/0866; A61B 8/4472; A61B 8/462; A61B 8/488;
(Continued)

(56) References Cited

U.S. PATENT DOCUMENTS 3,728,670 A * 4/1973 Rosauer ............... A61B 5/0275
367/94
4,089,044 A * 5/1978 Gatto .................. H01M 2/1022
361/625
(Continued)

FOREIGN PATENT DOCUMENTS

CN 101460094 A 6/2009
CN 202843648 U 4/2013
(Continued)

OTHER PUBLICATIONS

International Search Report and Written Opinion dated Jan. 8, 2018 for International Application No. PCT/CN2017/079972.
(Continued)

*Primary Examiner* — Peter Luong
(74) *Attorney, Agent, or Firm* — David D. Brush; Westman, Champlin & Koehler, P.A.

(57) ABSTRACT

A Doppler fetal heartbeat monitor includes: a housing; a mainboard; a loudspeaker installed in the housing and electrically connected to the mainboard; and an ultrasonic transducer installed in the housing, electrically connected to the mainboard, and comprising at least one transduction wafer configured to generate an impulse wave, in which the ultrasonic transducer is internally provided at a head end of the housing, and the loudspeaker and the mainboard are internally provided at a tail end of the housing. By arranging the loudspeaker, the mainboard and the ultrasonic transducer in the housing, the Doppler fetal heartbeat monitor can have a compact structure and a small volume. Moreover, it is possible to reduce positive feedback of a sound system and a probability of a self-excited whistle.

15 Claims, 8 Drawing Sheets

(51) Int. Cl.
*A61B 8/00* (2006.01)
*A61B 8/08* (2006.01)
*A61B 5/00* (2006.01)

(52) U.S. Cl.
CPC .......... *A61B 8/4444* (2013.01); *A61B 8/4472* (2013.01); *A61B 8/462* (2013.01); *A61B 8/488* (2013.01); *H05K 5/0008* (2013.01); *H05K 5/0017* (2013.01); *H05K 5/0086* (2013.01); *A61B 8/4427* (2013.01); *A61B 2503/02* (2013.01)

(58) Field of Classification Search
CPC .......... A61B 8/4427; A61B 2503/02; H05K 5/0017; H05K 5/0086; H05K 5/0008
See application file for complete search history.

(56) References Cited

U.S. PATENT DOCUMENTS

| | | | |
|---|---|---|---|
| 4,413,629 A * | 11/1983 | Durley, III | A61B 5/0011 600/453 |
| 5,509,416 A | 4/1996 | Wilmott | |
| 8,189,043 B2 * | 5/2012 | Schneider | A61B 1/00124 348/82 |
| 10,052,084 B2 | 8/2018 | Cho et al. | |
| 2005/0165310 A1 * | 7/2005 | Bindefeld | A61B 8/4472 600/453 |
| 2007/0276252 A1 | 11/2007 | Kolasa et al. | |
| 2008/0228095 A1 * | 9/2008 | Richardson | A61B 7/026 600/528 |

FOREIGN PATENT DOCUMENTS

| | | |
|---|---|---|
| CN | 203763120 U | 8/2014 |
| CN | 104414686 A | 3/2015 |
| CN | 204445944 U | 7/2015 |
| CN | 105748104 A | 7/2016 |
| CN | 205411216 U | 8/2016 |
| CN | 106793996 A | 5/2017 |
| WO | 2007030136 A1 | 3/2007 |
| WO | 2016207672 A2 | 12/2016 |

OTHER PUBLICATIONS

Supplementary European Search Report dated Mar. 3, 2019 for corresponding European Application No. 17790935.5.
English translation of Office Action dated Jun. 3, 2019 for corresponding Chinese Application No. 201780000996.8.
English translation of International Search Report dated Jan. 8, 2018 for International Application No. PCT/CN2017/079972.
English translation of Written Opinion of the International Searching Authority dated Jan. 8, 2018 for International Application No. PCT/CN2017/079972.

* cited by examiner

A-A

DOPPLER FETAL HEARTBEAT MONITOR

CROSS-REFERENCE TO RELATED APPLICATIONS

This Application is a Section 371 National Stage Application of International Application No. PCT/CN2017/079972, filed Apr. 10, 2017, and published as WO 2018/187915 Al, not in English, the entire contents of which is incorporated herein by reference.

FIELD

The present disclosure relates to a technical field of medical equipment, and particularly, to a Doppler fetal heartbeat monitor.

BACKGROUND

Doppler fetal heartbeat monitors have been widely applied in hospitals, community health service centers or other medical units, and gradually prevail in household applications, exhibiting a development trend of miniaturization and integral probe. Doppler fetal heartbeat monitors basically function to listen to a fetal heartbeat sound and display a fetal heartbeat rate, and a single detection of fetal heartbeat lasts 1 to 10 minutes. Detection of gestational age generally needs to cover the entire gestational range from a younger gestational age to an older gestational age, such that the Doppler fetal heartbeat monitor has a higher requirement on fetal heartbeat rate detection sensitivity than a common fetal monitoring device, especially for detection of the younger gestational age.

Based on an expected use requirement of fetal heartbeat detection, an integrated Doppler fetal heartbeat monitor needs an internal power supply generally in the form of a battery, a built-in loudspeaker to emit the fetal heartbeat sound, and a display screen to show the fetal heartbeat rate, such that a user can read the fetal heartbeat rate conveniently. The size of the integrated machine develops towards the miniaturization, but it is difficult to design an integrated Doppler fetal heartbeat monitor that can meet clinical use very well, due to relatively large dimensions of the loudspeaker, the display screen, the battery, and other limiting factors. Thus, there are many problems as follows: the integrated machine cannot achieve a miniaturized size, but appears very cumbersome, which is not convenient for the user to hold; and the Doppler fetal heartbeat monitor is encountered with a problem of producing a self-excited whistle, thereby affecting the clinical effect.

SUMMARY

Embodiments of the present disclosure seek to solve at least one of the problems existing in the related art to at least some extent. Accordingly, the present disclosure provides a Doppler fetal heartbeat monitor that has a compact structure and a small volume.

The Doppler fetal heartbeat monitor according to embodiments of the present disclosure includes: a housing; a mainboard; a loudspeaker installed in the housing and electrically connected to the mainboard; and an ultrasonic transducer installed in the housing, electrically connected to the mainboard, and including at least one transduction wafer configured to generate an impulse wave, in which the ultrasonic transducer is internally provided at a head end of the housing, and the loudspeaker and the mainboard are internally provided at a tail end of the housing.

For the Doppler fetal heartbeat monitor according to embodiments of the present disclosure, by arranging the loudspeaker, the mainboard and the ultrasonic transducer in the housing, an internal space utilization rate of the housing can be improved effectively, and the Doppler fetal heartbeat monitor can have the compact structure and the small volume. Additionally, in the embodiments of the present disclosure, the ultrasonic transducer and the loudspeaker are installed in the same installation space of the housing, and the ultrasonic transducer operates in an impulse wave mode, such that a probability of the self-excited whistle is reduced.

In some examples of the present disclosure, the housing includes a first chamber and a second chamber spaced apart therein; the mainboard and the loudspeaker are located in the first chamber, the loudspeaker is located at a first side of the mainboard in the first chamber; the ultrasonic transducer is located in the second chamber.

In some examples of the present disclosure, the housing includes an upper housing and a lower housing, the upper housing and the lower housing are provided with a partition plate separately, and the respective partition plates of the upper housing and the lower housing are disposed opposite to each other, so as to define the first chamber.

In some examples of the present disclosure, the housing further includes a head housing; the partition plates of the upper housing and the lower housing, along with the head housing, define the second chamber.

In some examples of the present disclosure, the lower housing includes a battery compartment recessed, and the recessed battery compartment is defined in the first chamber; the ultrasonic transducer and the loudspeaker are located at two sides of the battery compartment in a length direction of the housing respectively.

In some examples of the present disclosure, the Doppler fetal heartbeat monitor further includes a display screen electrically connected to the mainboard and located at a second side of the mainboard opposite to the first side in the first chamber.

In some examples of the present disclosure, the mainboard is connected with the ultrasonic transducer through a wire harness, and at least one of the respective partition plates of the upper housing and the lower housing is provided with a wire-passing hole.

In some examples of the present disclosure, the Doppler fetal heartbeat monitor further includes a fixing sleeve fitted over the loudspeaker and fixed to the lower housing, the lower housing being provided with a sound hole corresponding to the loudspeaker.

In some examples of the present disclosure, the lower housing includes a lower housing body defining a battery compartment; and a battery compartment cover body detachably mounted to the lower housing body.

In some examples of the present disclosure, respective inner surfaces of the upper housing and the lower housing are provided with a touch sensor separately, and the touch sensor is electrically connected with the mainboard.

In some examples of the present disclosure, the head housing is provided with a touch sensor, and the touch sensor is electrically connected with the mainboard.

In some examples of the present disclosure, the battery compartment is internally provided with a battery spring, the battery compartment is also provided with a battery spring bore, and a part of the battery spring extends out of the battery spring bore and is fixed to the mainboard by welding.

In some examples of the present disclosure, the mainboard is provided with a display screen support, and the display screen is fixed on the display screen support.

In some examples of the present disclosure, the mainboard is provided with an earphone socket, and the housing is provided with an earphone jack corresponding to the earphone socket.

In some examples of the present disclosure, the display screen corresponds to a display window formed in the upper housing.

In some examples of the present disclosure, the fixing sleeve is configured as a soft silicone rubber sleeve and binds with the lower housing.

REFERENCE NUMERALS

Figure 1:
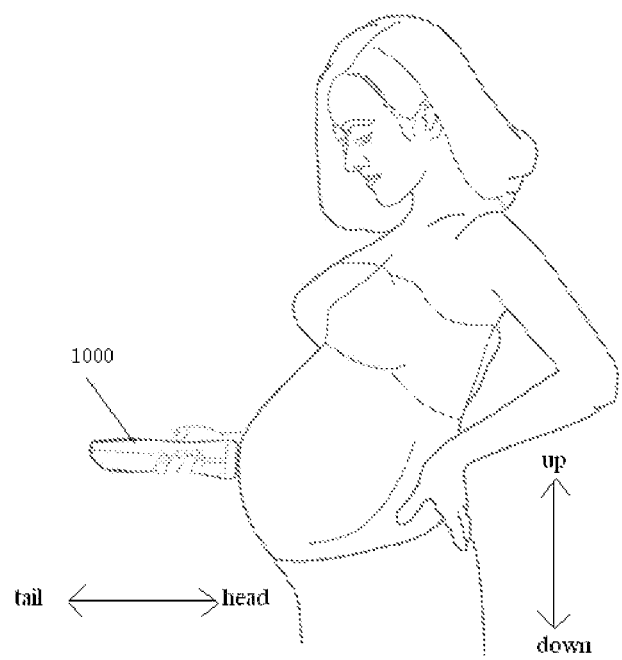
FIG. 1 illustrates a use state diagram of a Doppler fetal heartbeat monitor used by a user.

Doppler fetal heartbeat monitor 1000, housing 100, upper housing 110, display window 111, partition plate 112, wire-passing hole 113, key area 114, lower housing 120, battery compartment 121, sound hole 122, battery spring 123, battery spring bore 124, lower housing body 125, battery compartment cover body 126, sponge mat 127, head housing 130, holding portion 140, fixing sleeve 150, touch sensor 160, first chamber 170, second chamber 180, wire harness 190, mainboard 200, key 210, earphone socket 220, display screen 300, flexible circuit board 310, display screen support 320, dustproof ring 330, display panel 340, loudspeaker 400, ultrasonic transducer 500, ultrasonic emitting wafer 510, ultrasonic receiving wafer 520, battery 600.

DETAILED DESCRIPTION

Embodiments of the present disclosure will be described in detail, and examples of the embodiments will be illustrated in the accompanying drawings. The embodiments described herein with reference to the drawings are explanatory, which aim to explain the present disclosure, but shall not be construed to limit the present disclosure.

A Doppler fetal heartbeat monitor 1000 according to embodiments of the present disclosure will be described in detail with reference to FIGS. 1 to 12. It should be noted that the Doppler fetal heartbeat monitor 1000 herein has an integrated structure instead of a traditional split structure.

In some embodiments of the present disclosure, the Doppler fetal heartbeat monitor 1000 includes a housing 100, a mainboard 200, a loudspeaker 400 and an ultrasonic transducer 500. The loudspeaker 400 and the ultrasonic transducer 500 are installed in the housing 100; the ultrasonic transducer 500 includes at least one transduction wafer configured to generate an impulse wave; the loudspeaker 400 and the ultrasonic transducer 500 are both electrically connected to the mainboard 200. The ultrasonic transducer 500 is internally provided at a head end of the housing 100, and the loudspeaker 400 and the mainboard 200 are internally provided at a tail end of the housing 100.

It should be noted that orientations and positions of the Doppler fetal heartbeat monitor 100 according to embodiments of the present disclosure depend on an operating position shown in FIG. 1. A direction towards a user's head represents an upward direction, while a direction towards the user's foot represents a downward direction; a direction towards the user's abdomen represents the head end, while a direction away from the user's abdomen represents the tail end.

In some embodiments, the housing 100 includes a first chamber 170 and a second chamber 180 spaced apart therein. The mainboard 200 is provided in the first chamber of the housing 100, in which the mainboard 200 extends in the substantially same direction as the housing 100 extends, i.e. an extension direction between the head end and the tail end.

The loudspeaker 400 is electrically connected to the mainboard 200, and the loudspeaker 400 is located at a first side (e.g. a lower side) of the mainboard 200 in the first chamber. Under the drive of the mainboard 200, the loudspeaker 400 can emit a fetal heartbeat sound to improve user experience. In addition, since the loudspeaker 400 is located at the lower side of the mainboard 200, a space between the mainboard 200 and a lower inner surface of the housing 100 can be utilized reasonably, and a mutual collision between a display screen 300 and the loudspeaker 400 can be avoided to arrange the loudspeaker 400 in the housing 100 reasonably. Compared with the related art where a loudspeaker is connected to a main device via a cable and operates independently to broadcast a fetal heartbeat audio. The loudspeaker, the ultrasonic transducer and the mainboard are all arranged in the housing, thereby achieving an authentic integrated portable Doppler fetal heartbeat monitor, satisfying a requirement of household use, and facilitating realization of a miniaturization goal of the Doppler fetal heartbeat monitor 1000.

The ultrasonic transducer 500 is electrically connected to the mainboard 200, and the ultrasonic transducer 500 is located in the second chamber of the housing 100. The mainboard 200 can be configured to drive the ultrasonic transducer 500 to emit an ultrasonic wave, configured to amplify, demodulate and filter an ultrasonic Doppler signal picked up by the ultrasonic transducer 500, and configured to perform a fetal heartbeat rate calculation processing on fetal heartbeat data collected and drive the loudspeaker 400 to emit the fetal heartbeat sound.

The mainboard 200 can be provided with an ultrasonic module, a filtration and amplification module, a power module, and an audio power amplification module. The ultrasonic module is arranged at a position of the mainboard 200 adjacent to the ultrasonic transducer 500; the audio power amplification module is provided at a position of the loudspeaker 400; the filtration module is provided between the ultrasonic module and the audio power amplification module; the power module is provided at a position adjacent to a battery compartment 121. The arrangement of the above modules facilitates an overall layout of the mainboard 200, further improving internal space and product performance of the Doppler fetal heartbeat monitor 1000.

Furthermore, the ultrasonic transducer 500 is located at the head end of the housing 100 towards the human body. Thus, the ultrasonic transducer 500 can reasonably utilize a space at the head end in the housing 100, and can be utilized to emit the ultrasonic wave and receive the ultrasonic Doppler signal. In such a way, a distance between the loudspeaker 400 and the ultrasonic transducer 500 can also be increased at least to some extent, thereby reducing positive feedback of a sound system and the probability of a self-excited whistle.

Therefore, for the Doppler fetal heartbeat monitor 1000 according to embodiments of the present disclosure, by providing the display screen 300, the loudspeaker 400, the mainboard 200 and the ultrasonic transducer 500 in the housing 100, an internal space utilization rate of the housing 100 can be improved effectively, and the Doppler fetal heartbeat monitor 1000 can have a compact structure and a small volume. In addition, the distance between the loudspeaker 400 and the ultrasonic transducer 500 can also be increased at least to some extent, thereby reducing the positive feedback of the sound system and the probability of the self-excited whistle.

In some embodiments, the housing 100 defines the battery compartment 121 therein. Certainly, the housing 100 may be provided with other parts, for example, a holding portion 140 that may be held by the user's hand, such that the user can hold and operate the Doppler fetal heartbeat monitor 1000 conveniently. The battery compartment 121 can be configured to accommodate a battery 600 that serves as a power source of the Doppler fetal heartbeat monitor 1000. The ultrasonic transducer and the loudspeaker are located at two sides of the battery compartment in a length direction of the housing.

In some embodiments, the Doppler fetal heartbeat monitor further includes the display screen 300, the display screen 300 is electrically connected to the mainboard 200 and located at a second side (e.g. an upper side, particularly an upper surface) of the mainboard 200 opposite to the first side, and the display screen 300 corresponds to a display window 111. The display information of the display screen 300 can be presented to the user through the display window 111. Moreover, the display screen 300 thus provided can reasonably utilize a space between the mainboard 200 and an upper inner surface of the housing 100, and can reasonably arrange the display screen, thereby improving the internal space utilization rate of the housing 100 and facilitating realization of the miniaturization goal of the Doppler fetal heartbeat monitor 1000.

Figure 12:
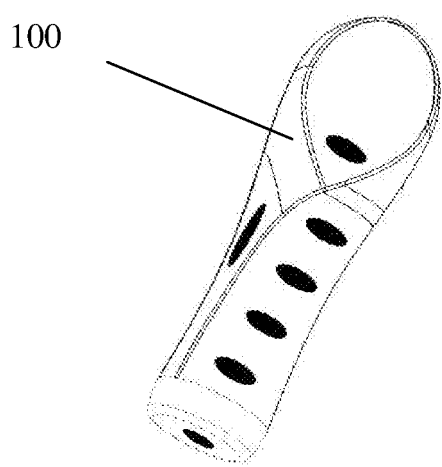
FIG. 12 illustrates a schematic view of a Doppler fetal heartbeat monitor according to still another embodiment of the present disclosure.

In some embodiments, the housing 100 is provided with the display window 111, and the display window 111 can be configured to display corresponding data, such as the fetal heartbeat rate, the number of fetal movement and so on. The display window 111 is located on an upper surface of the housing 100. In some embodiments of the present disclosure, the housing may not be provided with the display screen or the display window, as shown in FIG. 12.

Figure 2:
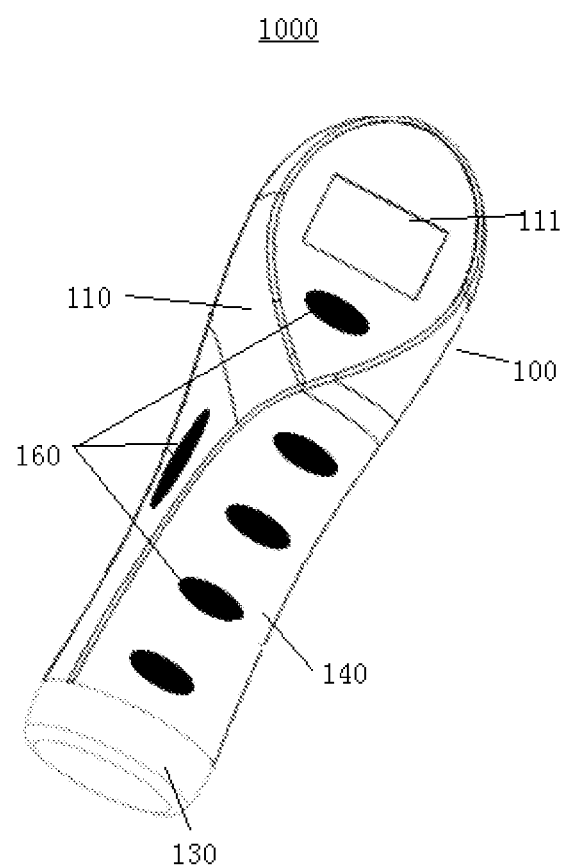
FIG. 2 illustrates a schematic view of a Doppler fetal heartbeat monitor according to an embodiment of the present disclosure.

Optionally, as shown in FIG. 2, the display window 111 can be provided away from the head end of the housing 100. For example, the display window 111 can be provided adjacent to the tail end of the housing 100 relative to the holding portion 140, in which the holding portion 140 of the housing 100 can be provided adjacent to the head end of the housing 100, such that it is convenient for the user to hold the Doppler fetal heartbeat monitor 1000 and observe the fetal heartbeat rate shown by the display window 111, i.e. a use state illustrated in FIG. 1, which brings great convenience to the user and helps the user experience.

The battery compartment 121 and the loudspeaker 400 are spaced apart in the length direction of the housing 100. It should be noted that the length direction of the housing 100 is the extension direction between the head end and the tail end illustrated in FIG. 1. Thus, the battery compartment 121 can be provided on the lower inner surface of the housing 100, so as to arrange the battery compartment 121 reasonably, utilize a space below the mainboard 200 reasonably, and achieve the miniaturization goal of the Doppler fetal heartbeat monitor 1000.

Figure 4:
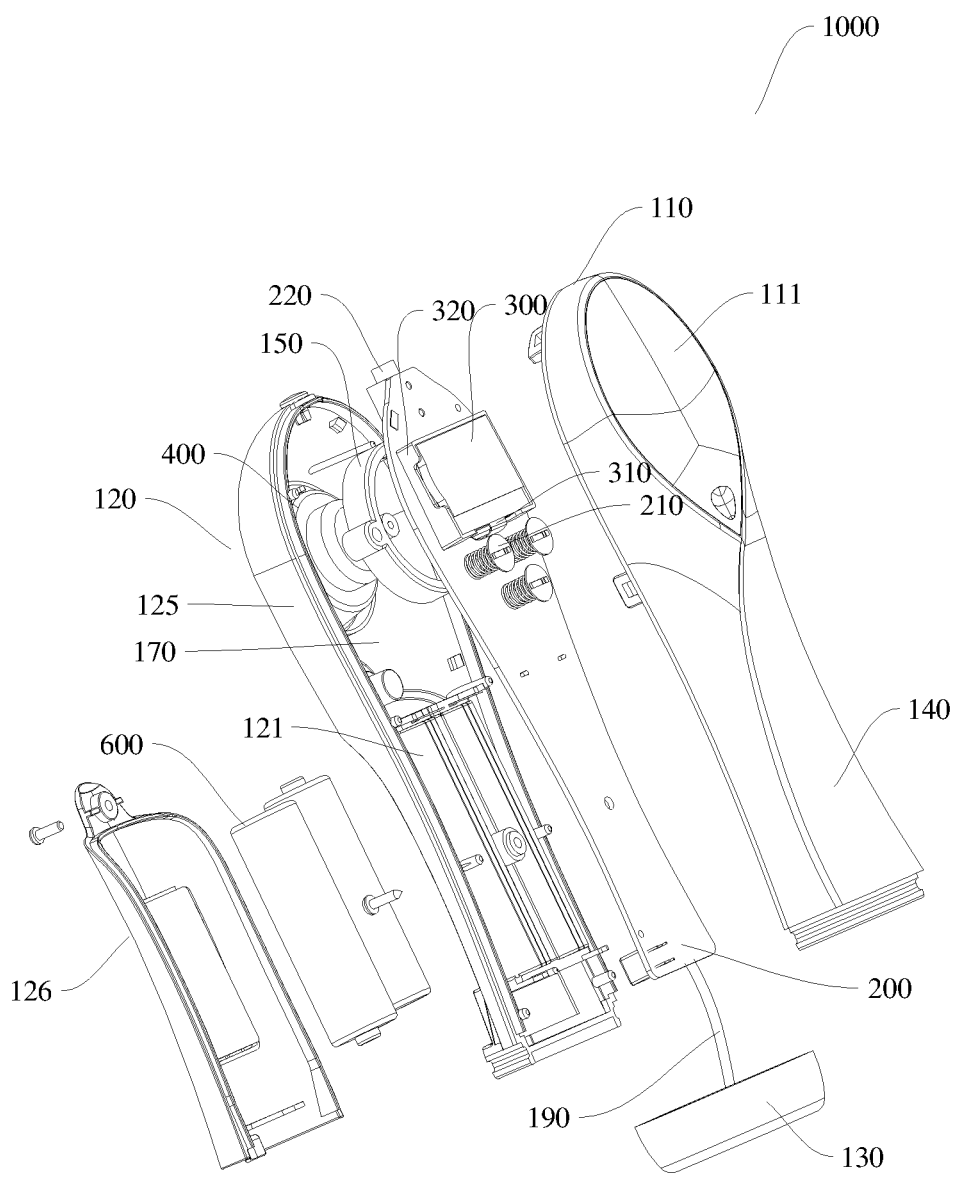
FIG. 4 illustrates an exploded view of a Doppler fetal heartbeat monitor according to an embodiment of the present disclosure.
Figure 5:
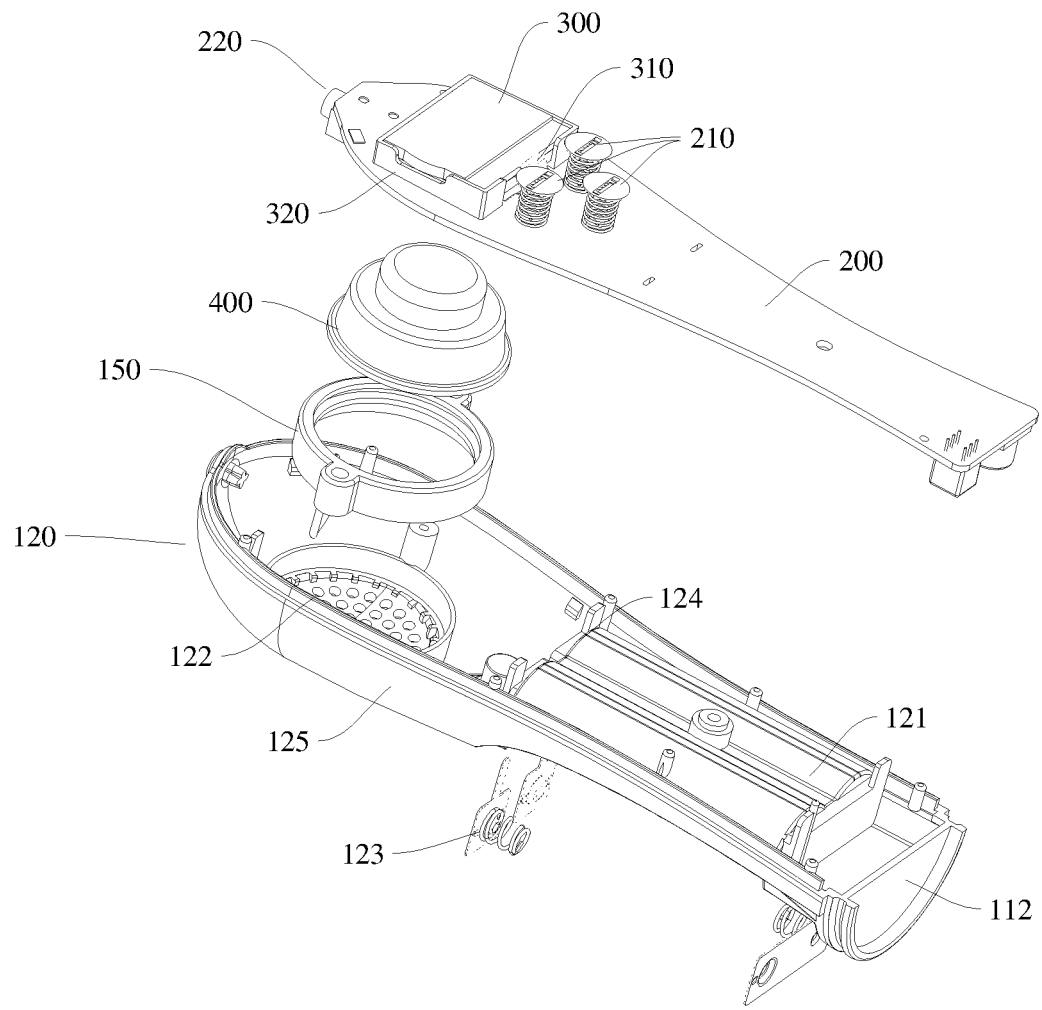
FIG. 5 illustrates a schematic view of a mainboard, a loudspeaker and a lower housing.

Further, as illustrated in FIGS. 4 and 5, the loudspeaker 400 can be provided away from the head end of the housing 100. In other words, the loudspeaker 400 can be provided away from the ultrasonic transducer 500, so as to reduce the positive feedback of the sound system, thereby lowering the probability of the self-excited whistle of the Doppler fetal heartbeat monitor 1000. In other embodiments, positions of the loudspeaker and the battery compartment can be exchanged.

As illustrated in FIG. 2, the housing 100 can be in a straight tube shape. The straight tubular housing 100 can be convenient for the user to hold on the one hand, and can facilitate arrangement of the mainboard 200 on the other hand, which can be conductive to achieving the miniaturization goal of the Doppler fetal heartbeat monitor 1000.

Optionally, as illustrated in FIG. 2, the upper surface of the housing 100 can be in a swaddle shape. In other words, a surface of the housing 100 towards the user's head has the swaddle shape, such that the user can observe and hold the Doppler fetal heartbeat monitor 1000 conveniently, which can satisfy operational characteristics of the user better and improve the user experience.

In other embodiments, the head end is not limited to a bottom position of the fetal heartbeat monitor, and can be at other positions of the fetal heartbeat monitor, as long as an end used to measure is the head end.

A specific arrangement form of the housing 100 will be described in detail with reference to FIGS. 4 and 5.

The housing 100 can include an upper housing 110, a lower housing 120 and a head housing 130. The display window 111 is formed in the upper housing 110, and the upper housing 110 can constitute the upper surface of the housing 100. The lower housing 120 and the upper housing 110 can be mounted opposite to each other. The way of mounting the upper housing 110 and the lower housing 120 is not limited. For example, respective inner edges of the upper housing 110 and the lower housing 120 can be provided with a snap-fit structure, such that the upper housing 110 and the lower housing 120 can be snapped and fixed; for another example, the upper housing 110 and the lower housing 120 can be internally provided with screw studs, and screws pass through corresponding screw studs to fix the upper housing 110 and the lower housing 120 together; for still another example, the upper housing 110 and the lower housing 120 can be fixed in the form of a combination of the above two fixing ways.

The upper housing 110 and the lower housing 120 define the first chamber 170, and the lower housing 120 includes the battery compartment 121 recessed, and the recessed battery compartment is defined in the first chamber 170 of a rear housing 120. The head housing 130 is mounted to and encloses head ends of the upper housing 110 and the lower housing 120, and the head housing 130 defines the second chamber 180 along with the upper housing 110 and the lower housing 120. Thus, the housing 100 can have a compact structure and better accommodate various internal parts. The head ends of the upper housing 110 and the lower housing 120 can be provided with external threads separately, and an inner circumferential wall of the head housing 130 can be provided with internal threads, such that the head housing 130 can be in threaded connection with the upper housing 110 and the lower housing 120, and the threaded connection achieves high efficiency of assembling the upper housing 110, the lower housing 120 and the head housing 130, and facilitates disassembly.

Figure 6:
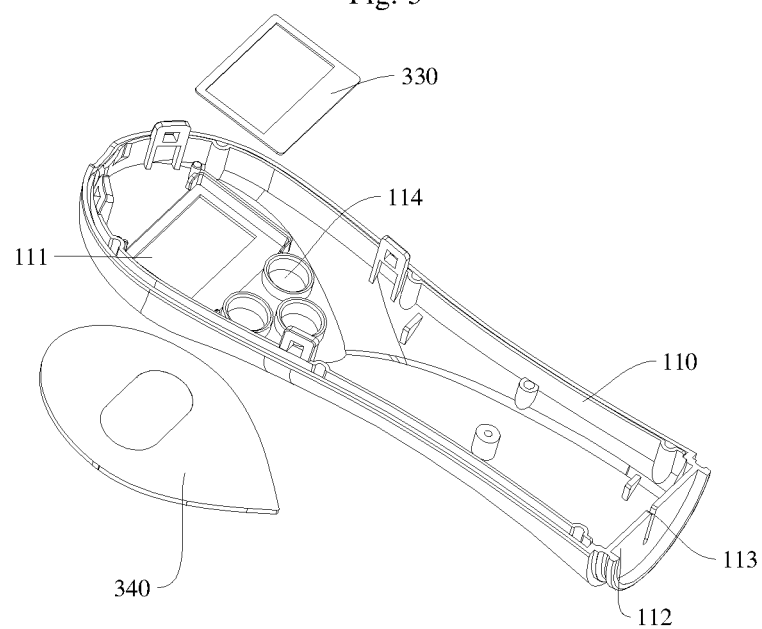
FIG. 6 illustrates a schematic view of an upper housing.

Further, as illustrated in FIGS. 5 and 6, the upper housing 110 and the lower housing 120 are provided with a partition plate 112 separately. Specifically, the partition plates 112 are provided at positions of respective inner surfaces of the upper housing 110 and the lower housing 120 adjacent to the head ends, and the respective partition plates 112 of the upper housing 110 and the lower housing 120 are disposed opposite to each other, so as to define the first chamber 170 between the upper housing 110 and the lower housing 120, and the partition plates 112, along with the head housing 130, define the second chamber 180. The mainboard 200, the display screen 300 and the loudspeaker 400 are accommodated in the first chamber 170, while the ultrasonic transducer 500 is accommodated in the second chamber 180. By providing the partition plates 112, the mainboard 200, the display screen 300, the loudspeaker 400 and the ultrasonic transducer 500 can be spaced apart effectively to further solve the problem of the self-excited whistle of the Doppler fetal heartbeat monitor 1000.

Specifically, the mainboard 200 can be connected with the ultrasonic transducer 500 through a wire harness 190, and at least one of the respective partition plates 112 of the upper housing 110 and the lower housing 120 is provided with a wire-passing hole 113. As illustrated in FIG. 6, in this embodiment, the wire-passing hole 113 is provided in the partition plate 112 of the upper housing 110, specifically in the middle of the partition plate, such that the wire harness can pass through the wire-passing hole 113 conveniently, and a length of the wire harness between the mainboard 200 and the ultrasonic transducer 500 can be relatively small, thereby facilitating the realization of the miniaturization goal of the Doppler fetal heartbeat monitor 1000. The partition plate 112 of the upper housing 110 can be provided with the wire-passing hole 113, while the partition plate 112 of the lower housing 120 may not be provided with the wire-passing hole 113, such that reliability of the wire harness in the wire-passing hole 113 can be ensured. In addition, by connecting the mainboard 200 and the ultrasonic transducer 500 by the wire harness, it is possible to facilitate stable and reliable transmission of an ultrasonic signal, avoid introducing noise into the fetal heartbeat sound due to shaking of a lead wire of the ultrasonic transducer 500, and further improve the product performance of the Doppler fetal heartbeat monitor 1000.

Figure 7:
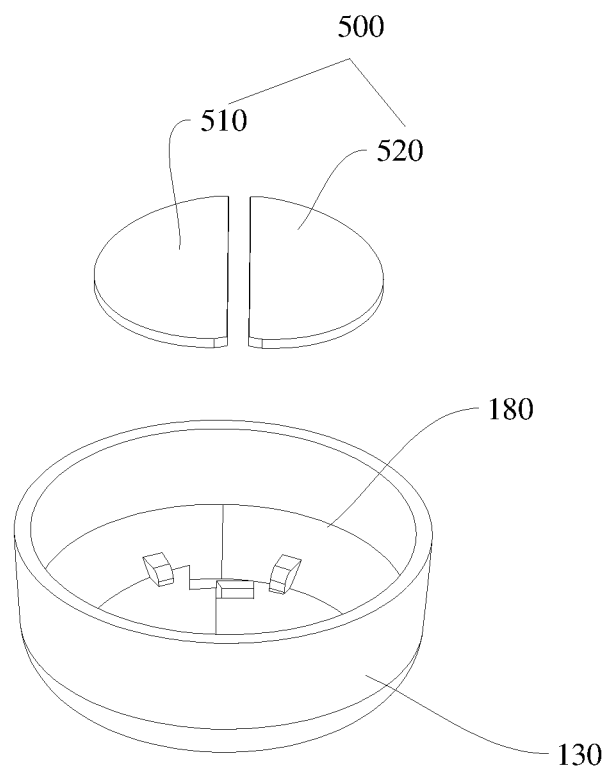
FIGS. 7 and 8 illustrate schematic views of two different kinds of ultrasonic transducers and head housings respectively.
Figure 8:
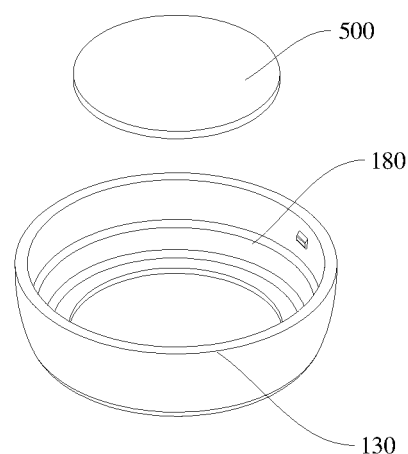

The ultrasonic transducer 500 can be arranged in various forms, which will be described in detail with reference to FIGS. 7 and 8.

An operation mode of the ultrasonic transducer in the related art generally employs continuous waves, i.e. an operation mode where an ultrasonic emitting transducer is used to emit the ultrasonic wave while an ultrasonic receiving transducer is used to receive a Doppler echo signal. However, in a miniaturized Doppler fetal heartbeat monitor, the operation mode of continuous waves generates the problem of self-excited whistle. In the present disclosure, the operation mode of the ultrasonic transducer is preferably an operation mode of impulse waves, i.e. the ultrasonic transducer can employ a time-sharing operation mode of ultrasonic emission and ultrasonic reception. Thus, it is possible to maximize an intersection range of an ultrasonic emission beam and an ultrasonic reception beam when a surface of the head housing 130 in contact with a belly of a pregnant woman is constant, so as to expand a fetal heartbeat detection range effectively without increasing a volume of a probe, thereby achieving the miniaturization goal. As illustrated in FIG. 8, the ultrasonic transducer 500 can be realized in the form of a single flat wafer or a spherical wafer, in which the spherical wafer facilitates further expansion of the fetal heartbeat detection range. Also, it is possible to adopt a form of multiple wafers in a parallel array. As illustrated in FIG. 7, the ultrasonic transducer 500 includes two semi-circular wafers, in which one wafer is an ultrasonic emitting wafer 510 while the other wafer is an ultrasonic receiving wafer 520, and an effective area of ultrasonic detection is an intersection range of ultrasonic beams of the two wafers. The head housing 130 can be internally provided with a support protrusion configured to support the two semi-circular wafers. The employment of impulse waves can expand the fetal heartbeat detection range and meanwhile avoid the problem of the self-excited whistle effectively, by correspondingly adjusting timing sequence between emission and reception, a fetal heartbeat detection depth can be controlled and noises in a superficial non-fetal heartbeat depth range can be filtered out effectively, thereby avoiding the self-excited whistle due to a superficial noise signal.

A way for fixing the loudspeaker 400 will be described in detail with reference to FIGS. 4 and 5.

Figure 10:
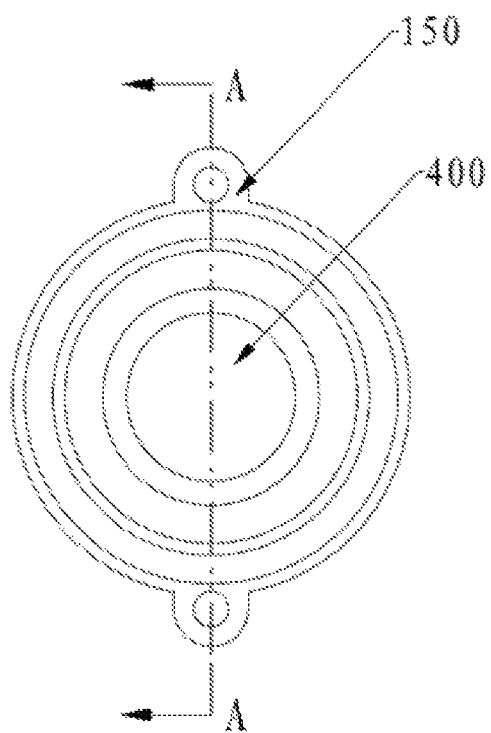
FIG. 10 illustrates a schematic view of a fixing sleeve and a loudspeaker.
Figure 11:
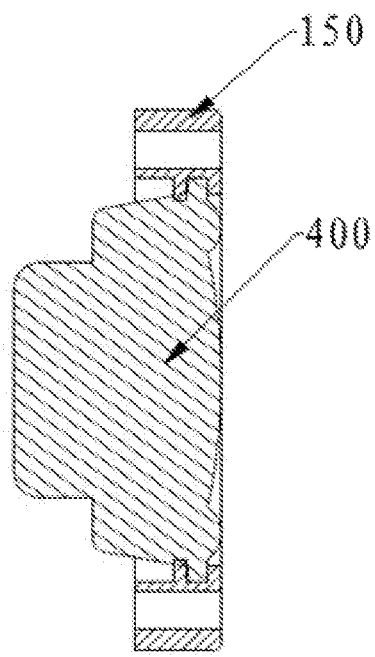
FIG. 11 illustrates a sectional view taken along line A-A of FIG. 10.

Specifically, the Doppler fetal heartbeat monitor 1000 can further include a fixing sleeve 150, and the fixing sleeve 150 is fitted over the loudspeaker 400. As illustrated in FIG. 10, the loudspeaker 400 has a lower edge, the fixing sleeve 150 can be provided with an annular groove, and the lower edge of the loudspeaker 400 can be entirely inserted into the annular groove, such that the annular groove can serve to mount and fix the lower edge of the loudspeaker 400. Additionally, the fixing sleeve 150 is fixed to the lower housing 120, and the lower housing 120 is provided with a sound hole 122 corresponding to the loudspeaker 400. In other words, the loudspeaker 400 can be fixed to the lower housing 120 through the fixing sleeve 150, so as to ensure the reliability of the loudspeaker 400 installed in the housing 100; furthermore, the loudspeaker 400 and the display screen 300 can be provided correspondingly to upper and lower sides of the mainboard 200, so as to utilize the internal space of the housing 100 more reasonably, thereby facilitating achievement of the miniaturization goal of the Doppler fetal heartbeat monitor 1000. Moreover, the sound hole 122 can facilitate audio output of the loudspeaker 400 to the outside, and hence the user can listen to the fetal heartbeat sound conveniently.

Further, the fixing sleeve 150 can be a soft silicone rubber sleeve. Thus, the fixing sleeve 150 can effectively achieve a damping effect, so as to reduce vibration of the housing 100 caused by sound vibration of the loudspeaker 400, thereby lowering the probability of the self-excited whistle of the Doppler fetal heartbeat monitor 1000 effectively.

The lower housing 120 may be provided with a screw hole, and a screw is fixed in the screw hole of the lower housing 120 after passing through the soft silicone rubber sleeve, such that the soft silicone rubber sleeve can be fixed to the lower housing 120 effectively and the reliability of fixing the loudspeaker 400 in the housing 100 can be ensured. The number of screws is not limited. For example, as illustrated in FIG. 5, two screws can be provided, and certainly, three, four or even more screws can be provided and distributed along a circumferential direction of the soft silicone rubber sleeve evenly. The fastening through two screws can miniaturize the internal space of the Doppler fetal heartbeat monitor 1000 when guaranteeing a fastening effect.

In addition, the provision of the soft silicone rubber sleeve can isolate a front sound cavity from a rear sound cavity of the loudspeaker 400 effectively, to avoid an acoustic short-circuit between the front sound cavity and the rear sound cavity, improve electro-acoustic conversion efficiency, and optimize the fetal heartbeat sound quality, which further can be conducive to emitting and broadcasting the fetal heartbeat sound.

Furthermore, the provision of the soft silicone rubber sleeve can also enhance a waterproof design, such that liquid water can only enter the front sound cavity of the loudspeaker 400 and cannot enter the Doppler fetal heartbeat monitor 1000 through the soft silicone rubber, thereby further improving waterproof performance of the Doppler fetal heartbeat monitor 1000.

Moreover, in the case of the fixing sleeve 150 being the soft silicone rubber sleeve, the fixing sleeve 150 can bind with the lower housing 120. It is possible to directly bind the soft silicone rubber sleeve to the lower housing 120 without using the screws for fixation, and hence the internal space of the Doppler fetal heartbeat monitor 1000 can be further miniaturized.

Additionally, in other embodiments, the loudspeaker 400 can be directly fixed to the lower housing 120 by screws or binding.

An arrangement form of the battery compartment 121 will be described in detail with reference to FIGS. 4 and 5.

Optionally, the battery compartment 121 is defined at a position of the lower housing 120 adjacent to the head end of the housing 100. Thus, the battery compartment 121 can isolate the loudspeaker 400 from the ultrasonic transducer 500 effectively, further lowering the probability of the self-excited whistle of the Doppler fetal heartbeat monitor 1000; and a space at the lower housing 120 can be utilized reasonably, which makes the structure of the Doppler fetal heartbeat monitor 1000 compact and the volume thereof small.

Further, as illustrated in FIG. 5, the battery compartment 121 can be internally provided with a battery spring 123, and the battery compartment 121 can also be provided with a battery spring bore 124. A part of the battery spring 123 extends out of the battery spring bore 124 and fixed to the mainboard 200 by welding. The mainboard 200 can be provided with a bonding pad hole, and the part of the battery spring 123 is fixed to the bonding pad hole by welding. It should be noted that the part of the battery spring 123 extends into the housing 100 from an outer side of the lower housing 120, and then is fixed to the bonding pad hole in the mainboard 200 by welding, so as to fix the lower housing 120 and the mainboard 200 at least to a certain extent and enhance the reliability of the mainboard 200 installed in the housing 100. Furthermore, connection wires can be omitted to avoid messy connection wires in the Doppler fetal heartbeat monitor 1000, so as to further reduce the internal space of the Doppler fetal heartbeat monitor 1000 while ensuring the connection reliability, thereby further enhancing the product performance of the Doppler fetal heartbeat monitor 1000. Positive and negative springs of the battery 600 can be clamped and fixed to the lower housing 120 by direct snapping.

The lower housing 120 can also be fixed to the mainboard 200 by snapping, and the lower housing 120 can also be fixed to the mainboard 200 by screws.

Figure 9:
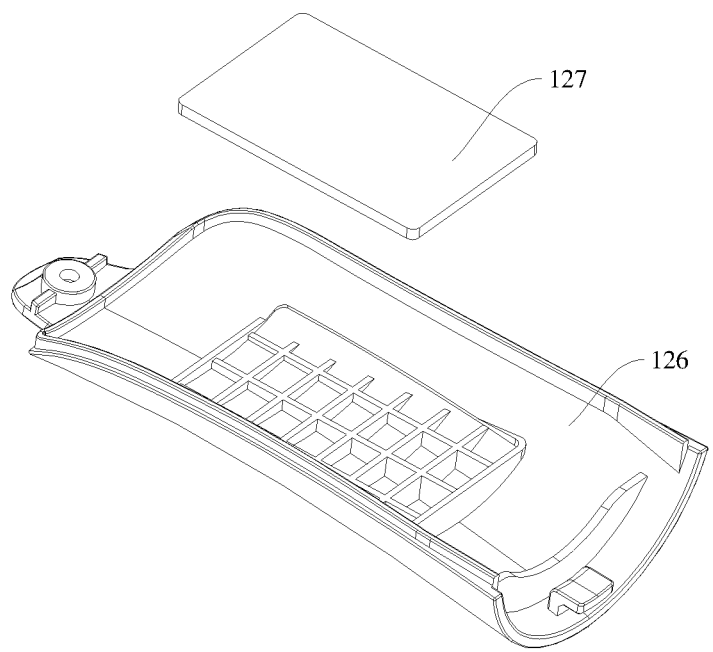
FIG. 9 illustrates a schematic view of a battery compartment cover body and a sponge mat.

It should be noted that a structure of the lower housing 120 needs to be selected and adjusted according to the battery 600. For example, if the battery 600 is selected to be a non-rechargeable battery, a battery compartment cover body 126 needs to be provided to facilitate installation and detachment of the battery 600. Specifically, as illustrated in FIGS. 4 and 9, the lower housing 120 can include a lower housing body 125 and the battery compartment cover body 126, the battery compartment cover body 126 can be detachably mounted to the lower housing body 125, and the battery compartment cover body 126 and the lower housing body 125 together define the battery compartment 121. During replacement of the battery 600, the user can detach the battery compartment cover body 126 from the lower housing body 125. It should be noted that as illustrated in FIG. 9, the battery compartment cover body 126 can be provided with a sponge pad 127 to protect the battery 600 and the battery compartment cover body 126 effectively.

For another example, if the battery 600 is selected to be a rechargeable battery, the rechargeable battery is provided within the Doppler fetal heartbeat monitor 1000 without the need to provide the battery compartment cover body 126, such that the overall design of the Doppler fetal heartbeat monitor 1000 is not destroyed, which can not only reduce the internal space of the Doppler fetal heartbeat monitor 1000 but also improve a waterproof grade of the Doppler fetal heartbeat monitor 1000.

A control form of the Doppler fetal heartbeat monitor 1000 will be described in detail with reference to FIG. 2.

Optionally, as illustrated in FIG. 2, respective inner surfaces of the upper housing 110 and the lower housing 120 are provided with a touch sensor 160, and the touch sensor 160 is electrically connected with the mainboard 200, in which the touch sensor 160 can be in a substantially oblong shape. When the user touches the touch sensor 160, the touch sensor 160 can generate an induction signal that triggers the device to turn on or turn off. Thus, it is attainable that the device turns on when the user holds and touches the device, and the device turns off automatically when the device leaves from the human body, so as to simplify an on/off operation of the Doppler fetal heartbeat monitor 1000 considerably, making the Doppler fetal heartbeat monitor 1000 intelligent, and save electric quantity of the battery 600 effectively, extending the endurance time of the battery 600.

Additionally, the Doppler fetal heartbeat monitor 1000 thus provided can be aesthetic and durable and has low costs. The entire machine may not be provided with any mechanical key, thus protecting integrity of the overall structure, achieving an effective waterproof design, avoiding attenuation or loss of a fetal heartbeat signal due to vibration of the device caused by operation of keys, and improving the detection reliability of the device greatly.

A plurality of touch sensors 160 can be connected in parallel, i.e. electrically connected as a whole. The plurality of touch sensors 160 can be arranged in different parts of the housing 100, e.g. front, rear, left and right portions, such that it is ensured that the touch sensor 160 is available to be touched when the user holds the holding portion 140. The touch sensor 160 can be attached to an inner surface of the housing 100, and the touch sensor 160 can realize its inductive function by means of a copper foil, a conductive sponge or a touch spring.

Figure 3:
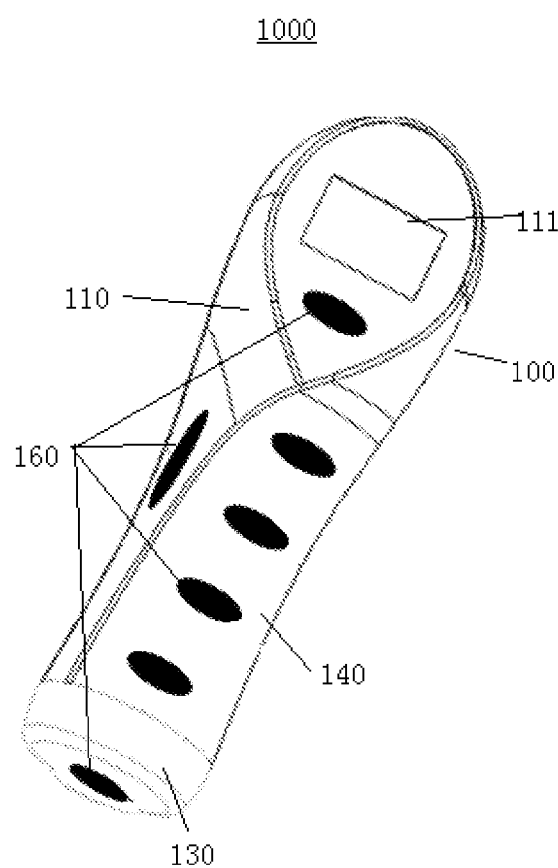
FIG. 3 illustrates a schematic view of a Doppler fetal heartbeat monitor according to another embodiment of the present disclosure.

Optionally, as illustrated in FIG. 3, the head housing 130 can be provided with the touch sensor 160, and the touch sensor 160 is electrically connected with the mainboard 200, except which FIG. 3 is identical to FIG. 2. It could be understood that the touch sensor 160 located at the head housing 130 can be used to identify whether the head housing 130 is in contact with the user's belly. Whether the head housing 130 contacts the user's belly will cause the touch sensor 160 to produce a corresponding touch signal, and the touch signal can control whether the ultrasonic module of the mainboard 200 to operate. When the Doppler fetal heartbeat monitor 1000 is in contact with the belly of the pregnant woman, the ultrasonic module of the mainboard 200 is controlled to operate; when the Doppler fetal heartbeat monitor 1000 is not in contact with the belly of the pregnant woman, the mainboard 200 is controlled to stop operation. Hence, it is possible to prolong service life of the ultrasonic transducer 500 effectively, reduce ultrasonic radiation, and further enhance an endurance ability of the Doppler fetal heartbeat monitor 1000.

An arrangement form of the display screen 300 will be described in detail with reference to FIGS. 4 to 6.

Optionally, the display screen 300 can be connected to the mainboard 200 through a conductive rubber connector. The conductive rubber connector can make the electrical connection between the display screen 300 and the mainboard 200 reliable and make the display screen 300 display data stably.

Optionally, as illustrated in FIG. 4, the display screen 300 can be connected to the mainboard 200 through a flexible circuit board 310. The flexible circuit board 310 can be directly welded to the mainboard 200, so as to further reduce the internal space of the Doppler fetal heartbeat monitor 1000 and further improve the reliability and stability of the electrical connection between the display screen 300 and the mainboard 200, thereby facilitating effective and stable transmission of the displayed signal.

Specifically, as illustrated in FIGS. 4 and 5, the mainboard 200 can be provided with a display screen support 320, and the display screen 300 is fixed on the display screen support 320. The conductive rubber connector or a part of the flexible circuit board 310 can be accommodated in a lower space of the display screen support 320, so as to reduce the space occupied by the display screen 300. The display screen support 320 can serve to fix the display screen 300 to the mainboard 200, so as to improve the reliability and stability of the electrical connection between the mainboard 200 and the display screen 300 and facilitate the effective and stable transmission of the displayed signal. Furthermore, if a fixing way of the conductive rubber connector in combination with the display screen support 320 is employed, the internal space of the Doppler fetal heartbeat monitor 1000 can be reduced effectively, thus facilitating the miniaturization design of the Doppler fetal heartbeat monitor 1000.

According to an optional embodiment of the present disclosure, as illustrated in FIG. 6, a dustproof ring 330 is provided and extends along a circumferential direction of the display screen 300. The dustproof ring 330 can be attached to the circumferential direction of the display screen 300 to prevent dust from entering the display screen 300 effectively, so as to enhance a display effect of the display screen 300. The dustproof ring 330 can be configured as a sponge ring for the display screen.

Also, as illustrated in FIG. 6, a display panel 340 can be provided at the display window 111, and the display panel 340 is provided with a transparent display area, such that information displayed by the display screen 300 can be presented through the display window 111 and the display panel 340, and the user can read the information of the display screen 300 conveniently and effectively.

Optionally, as illustrated in FIGS. 4 to 6, the mainboard 200 can be provided with a plurality of keys 210, the inner surface of the housing 100 can be provided with a plurality of key areas 114, and the plurality of keys 210 are disposed corresponding to the plurality of key areas 114. For example, three keys 210 can be provided, three key areas 114 can be provided, and the three keys 210 and the three key areas 114 are disposed in one-to-one correspondence. The above plurality of keys 210 can have an on/off function and a fetal heartbeat sound volume adjustment function respectively.

Further, the key 210 can be realized in the form of a touch key. Thus, the key 210 can adopt a touch spring or a conductive sponge, and the mainboard 200 can be internally provided with the touch drive module, so as to realize a function of the touch key effectively. The realization of the key 210 in the form of the touch key can not only protect the configuration, maintaining the structural integrity of the Doppler fetal heartbeat monitor 1000, but also enhance the waterproof performance of the Doppler fetal heartbeat monitor 1000; meanwhile, the touch key does not produce vibration as the mechanical key is operated, so as to effectively avoid deviation from the fetal heartbeat position due to vibration caused by the operation of the key 210 during the fetal heartbeat detection, which otherwise will lead to loss of the fetal heartbeat sound. Thus, the clinical use effect can be improved greatly.

Other functions and structures for implementing corresponding functions of the Doppler fetal heartbeat monitor 1000 will be elaborated below.

Optionally, the mainboard 200 can be provided with a wireless module. For example, by means of wireless connections such as Bluetooth or Wi-Fi, the user can wirelessly connect software of an intelligent device (e.g. a mobile phone or a tablet computer) to conduct the fetal heartbeat detection. A wireless antenna can be provided at the tail end of the Doppler fetal heartbeat monitor 1000, i.e. at a position away from the head end of the housing 100, so as to achieve the best effect of wireless transmission and the stability and reliability of wireless signal transmission.

Optionally, as illustrated in FIGS. 4 and 5, the mainboard 200 can be provided with an earphone socket 220, and the housing 100 can be provided with an earphone jack corresponding to the earphone socket 220, in which the earphone jack can be provided at the tail end of the housing 100. Thus, the user can listen to the fetal heartbeat sound in a noisy environment through an earphone, which further improves the user experience; by providing the earphone jack at the tail end of the housing 100, the normal fetal heartbeat detection is not interference while the user can hold and operate the fetal heartbeat monitor conveniently.

Reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, the appearances of the phrases throughout this specification are not necessarily referring to the same embodiment or example of the present disclosure. In addition, the particular features, structures, materials, or characteristics may be combined in any suitable manner in one or more embodiments or examples. Furthermore, different embodiments or examples, and features of the different embodiments or examples can be combined by those skilled in the art in the case of no contradiction.

Although embodiments have been illustrated and described, it would be appreciated by those skilled in the art that the above embodiments are explanatory and cannot be construed to limit the present disclosure, and changes, modifications, alternatives and variations can be made in the embodiments without departing from the scope of the present disclosure.

What is claimed is:

1. A Doppler fetal heartbeat monitor, comprising:
   a housing;
   a mainboard;
   a loudspeaker installed in the housing and electrically connected to the mainboard; and
   an ultrasonic transducer installed in the housing, electrically connected to the mainboard, and comprising at least one transduction wafer configured to generate an impulse wave,
   wherein the ultrasonic transducer is internally provided at a head end of the housing, and the loudspeaker and the mainboard are internally provided at a tail end of the housing,
   wherein the housing comprises an upper housing and a lower housing detachably connected to each other, the upper housing and the lower housing are provided with a partition plate separately, and the respective partition plates of the upper housing and the lower housing are disposed opposite to each other, so as to define a first chamber.

2. The Doppler fetal heartbeat monitor according to claim 1, wherein the housing comprises the first chamber and a second chamber spaced apart therein; the mainboard and the loudspeaker are located in the first chamber, the loudspeaker is located at a first side of the mainboard in the first chamber; the ultrasonic transducer is located in the second chamber.

3. The Doppler fetal heartbeat monitor according to claim 1, wherein the housing further comprises a head housing; the partition plates of the upper housing and the lower housing, along with the head housing, define the second chamber.

4. The Doppler fetal heartbeat monitor according to claim 3, wherein the head housing is provided with a touch sensor, and the touch sensor is electrically connected with the mainboard.

5. The Doppler fetal heartbeat monitor according to claim 1, wherein the lower housing comprises a battery compartment recessed, and the recessed battery compartment is defined in the first chamber;
   the ultrasonic transducer and the loudspeaker are located at two sides of the battery compartment in a length direction of the housing respectively.

6. The Doppler fetal heartbeat monitor according to claim 5, wherein the battery compartment is internally provided with a battery spring, the battery compartment is also provided with a battery spring bore, and a part of the battery spring extends out of the battery spring bore and is fixed to the mainboard by welding.

7. The Doppler fetal heartbeat monitor according to claim 1, further comprising a display screen electrically connected to the mainboard and located at a second side of the mainboard opposite to the first side in the first chamber.

8. The Doppler fetal heartbeat monitor according to claim 7, wherein the mainboard is provided with a display screen support, and the display screen is fixed on the display screen support.

9. The Doppler fetal heartbeat monitor according to claim 7, wherein the display screen corresponds to a display window formed in the upper housing.

10. The Doppler fetal heartbeat monitor according to claim 1, wherein the mainboard is connected with the ultrasonic transducer through a wire harness, and at least one of the respective partition plates of the upper housing and the lower housing is provided with a wire-passing hole.

11. The Doppler fetal heartbeat monitor according to claim 1, further comprising a fixing sleeve fitted over the loudspeaker and fixed to the lower housing, the lower housing being provided with a sound hole corresponding to the loudspeaker.

12. The Doppler fetal heartbeat monitor according to claim 11, wherein the loudspeaker has a lower edge, the fixing sleeve is provided with an annular groove, and the lower edge of the loudspeaker is entirely inserted into the annular groove.

13. The Doppler fetal heartbeat monitor according to claim 1, wherein the lower housing comprises a lower housing body defining a battery compartment; and a battery compartment cover body detachably mounted to the lower housing body.

14. The Doppler fetal heartbeat monitor according to claim 1, wherein respective inner surfaces of the upper housing and the lower housing are provided with a touch sensor separately, and the touch sensor is electrically connected with the mainboard.

15. The Doppler fetal heartbeat monitor according to claim 1, wherein the mainboard is provided with an earphone socket, and the housing is provided with an earphone jack corresponding to the earphone socket.

* * * * *